(12) United States Patent
Johnson et al.

(10) Patent No.: US 7,035,698 B2
(45) Date of Patent: Apr. 25, 2006

(54) SYSTEM FOR CONTROLLING MEDICAL IMAGING EQUIPMENT MOTION

(75) Inventors: Mark A. Johnson, Crete, NE (US); Luc Mauvarin, Chaville (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/898,039

(22) Filed: Jul. 23, 2004

(65) Prior Publication Data
US 2005/0004688 A1 Jan. 6, 2005

Related U.S. Application Data

(62) Division of application No. 09/973,588, filed on Oct. 9, 2001, now Pat. No. 6,785,578.

(51) Int. Cl.
*G05B 19/18* (2006.01)
(52) U.S. Cl. .................... 700/59; 600/409; 600/535; 73/514.16; 73/514.19; 73/514.25; 73/514.26; 73/514.31; 73/514.32
(58) Field of Classification Search ............. 600/409, 600/535; 73/514.16, 514.19, 514.25, 514.26, 73/514.31, 514.32, 514.33, 514.34; 700/59
See application file for complete search history.

(56) References Cited

U.S. PATENT DOCUMENTS 5,805,664 A * 9/1998 Whipple et al. ............ 378/117
6,025,562 A * 2/2000 Shimizu et al. ......... 174/17 SF
6,650,111 B1 * 11/2003 Christensen ........... 324/207.26

OTHER PUBLICATIONS

Jeon et al. "New Design of Cylindrical Capacitive Sensor for On-line Precision Control of AMB Spindle", Jun. 2001, IEEE Transactions on vol. 50 Issue 3, pp. 757-763.*
Chavan et al. "A monolithic fully-integrated vacuum-sealed CMOS pressure sensor", 2000, IEEE, pp 341-346.*
Li et al. "An accurate low-cost capacitive absolute angular-position sensor with a full-circle range", Apr. 1996, IEEE Transaction on vol. 45, pp 516-520.*
Frederick W. Hintz and James P. Bobis "Development of finite design simulation tool for proximity sensor coils with ferrite cores", May 1997, Instrumentation and Measurement Technology Conference, 1997 IEEE Proceedings, vol. 1, pp. 139-145.*
Kofi D. Anim-Appiah and Sedki M. Riad, "Analysis and Design of Ferrite Cores for Eddy-Current-Killed Oscillator Inductive Proximity Sensors", May 1997, IEEE Transactions, pp. 2274-2281.*

* cited by examiner

*Primary Examiner*—Anthony Knight
*Assistant Examiner*—Thomas Pham
(74) *Attorney, Agent, or Firm*—Armstrong Teasdale LLP

(57) ABSTRACT

A system including a user input device for controlling a position of medical equipment is described. In an example embodiment, the user input device is configured to be coupled to the medical equipment and is responsive to an operator input representation of a desired movement of the equipment. A processor determines a direction in which the operator desires the equipment to move based on a device output.

11 Claims, 7 Drawing Sheets

SYSTEM FOR CONTROLLING MEDICAL IMAGING EQUIPMENT MOTION

This application is a divisional of U.S. application Ser. No. 09/973,588, filed Oct. 9, 2001, which is hereby incorporated by reference. Now U.S. Pat. No. 6,785,578

BACKGROUND OF THE INVENTION

This invention relates generally to medical imaging, and more particularly, to positioning imaging components around a patient.

Diagnostic medical imaging requires accurate positioning of imaging equipment around a patient. Depending on the size and complexity of the equipment, the equipment can be positioned manually (e.g. dental X-rays) or through motorization of the equipment. With manual positioning, the operator has full control over the device being positioned and is restricted only by the range of motion of the equipment. Moreover, manually moving equipment is intuitive since one merely pushes and pulls the equipment into the desired location.

Some imaging equipment is motorized in order to help the operator move heavier equipment, or to facilitate advanced procedures in which the equipment must be precisely positioned or moved during an imaging procedure. The user device for control of larger motorized equipment typically is a joystick or a force input device (e.g. a spring-loaded handle with 1 to 3 degrees of freedom that measures the force applied to the handle). The joystick or force input devices are often located remotely from the equipment (e.g. on a user control panel) and have no particular relationship to the geometry of the machine. For example, left-right motion of the joystick may result in something other than left-right motion of the machine. Force input devices are sometimes attached directly to the device being controlled, and a force applied to the input device results in machine motion in the same direction as the applied force and a magnitude commensurate with the applied force.

In screening applications (e.g. mammography), there is a high-throughput of patients per day. Minimizing the time required for a particular exam, thus maximizing equipment and operator productivity, is highly desirable. In interventional applications (e.g. vascular X-ray), focused attention is on the patient and the medical procedure, and the control of the imaging device should be as intuitive, effortless, and efficient as possible.

BRIEF SUMMARY OF THE INVENTION

In one aspect, a system for controlling the position of medical equipment is provided. The system, in an example embodiment, comprises at least one sensor configured to be coupled to the medical equipment and responsive to an operator input representation of a desired movement of the equipment, and a processor coupled to the sensor for determining a direction in which the operator desires the equipment to move based on a sensor output.

In another aspect, a sensor comprising a core having an outer surface and a plurality of sensing areas on the outer surface is provided. Each sensing area is responsive to operator input for generating a signal representative of the operator input.

In yet another aspect, a medical imaging system is provided. In an example embodiment, the system comprises a source for transmitting signals towards a patient, a detector for detecting signals that have been transmitted through the patient, a movable member on which at least one of the source and the detector are mounted, and a user input device for controlling a position of the movable members. The user input device comprises a plurality of sensors coupled to the movable members and responsive to an operator input representation of a desired movement of the equipment. The system further comprises a processor coupled to the user input device for determining a direction in which the operator desires the member to move based on sensor outputs.

DETAILED DESCRIPTION OF THE INVENTION

The systems and methods described below are directed to operator control of medical imaging equipment position. Generally, multiple proximity sensors are located on the machine to be controlled. The outputs of the sensors are processed using a vectorial addition method to determine how the machine should move in response to an operator input. Moreover, in addition to detecting and processing operator inputs, the proximity of foreign objects (e.g. auxiliary equipment, the patient) is detected. Therefore, the equipment can be moved in a manner that attempts to satisfy the operator input as well as avoids collisions with surrounding objects.

The systems and methods described herein are based on capacitance sensors. Other non-contact proximity sensors, such as infrared or ultrasonic sensors, can be used. Capacitance sensors, however, have a simple construction and output, are not expensive, and facilitate easy customization of sensing zones by merely positioning conducting surfaces (e.g. a conductive material such as copper foil) to define the zones. Further, the systems and methods can also be used in contact based applications.

The systems and methods described herein can be used in connection with many different types of medical imaging systems. By way of example, set forth below is a description of one type of X-ray imaging system 10, illustrated in FIG. 1. Again, system 10 is described herein as an example only, and the systems and methods described herein can be used in connection with many different types of medical imaging systems, e.g., X-ray, computed tomography, magnetic resonance, positron emission tomography, and ultrasound.

Figure 1:
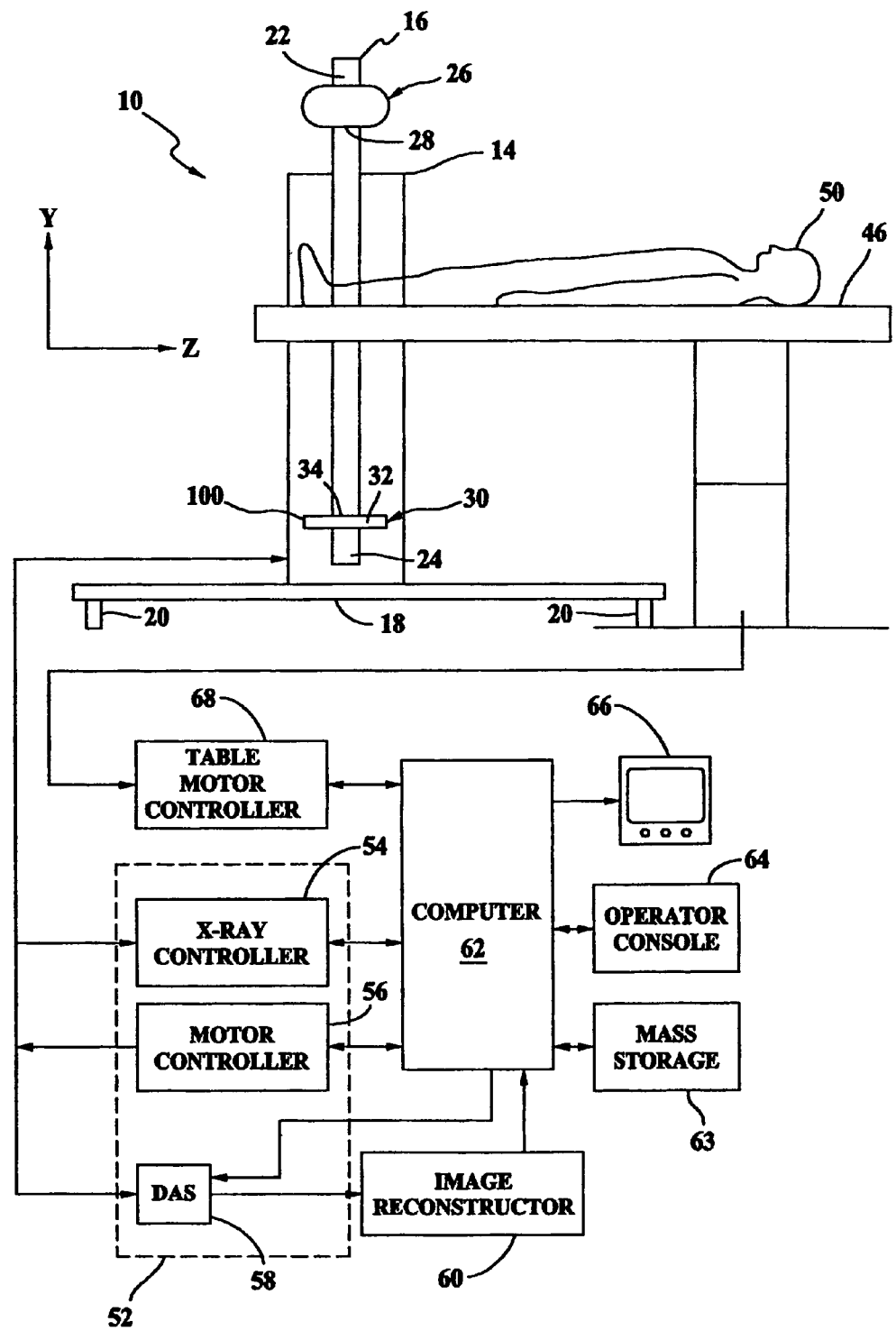
FIG. 1 is a schematic illustration of an X-ray imaging system.

More specifically, and referring to FIG. 1, imaging system 10 is shown as including a base 14 and a positioning arm 16. Base 14 extends from a portable platform 18 having a plurality of wheels 20 so that base 14 is movable relative to an object or patient 50 to be imaged. Rather than wheels 20, other position altering devices can be employed. For example, a pivot can be provided to allow tilting and rotating arm 16 of the imaging equipment.

Arm 16 includes a first end portion 22 and a second end portion 24. More specifically, arm 16 rotates relative to base 14 about an axis of rotation and moves relative to base 14 to alter the respective distances between arm first end portion 22 and base 14 and arm second end portion 24 and base 14.

An x-ray source assembly 26 is movably coupled to arm first end portion 22. X-ray source assembly 26 includes an X-ray source 28 configured to emit x-ray signals. A detector assembly 30 is movably coupled to arm second end portion 24. Detector assembly 30 includes a detector 32 configured to receive the x-ray signals from said source 28 to generate an image of the object. Detector 32 can be moved up and down using a motorized control.

By moving arm 16 relative to base 14, the position of source assembly 26 may be altered so that source assembly 26 is moved toward or away from base 14. Altering the position of source assembly 26, alters the position of detector assembly 30 relative to base 14 in an opposite direction. The orientation of assembly 26 and assembly 30 to the patient affects the image generated.

Detector 32, in one embodiment, is formed by a plurality of detector elements 34 which together sense projected x-rays that pass through an object. In the example embodiment, detector 32 is a flat panel, an image intensifier, or film. In one embodiment, detector 32 is a solid state detector or radiation imager comprising a large flat panel imaging device having a plurality of pixels 34 arranged in rows and columns. Again, the systems and methods described herein are not limited to use with any one particular type of detector.

System 10 also includes a table 46 for supporting patient 50. To generate an image of patient 50, arm 16 is rotated so that source assembly 26 and detector assembly 30 rotate about patient 50. More specifically, arm 16 is rotatably coupled to base 14 so that detector 32 and source 28 are rotated about object 50.

Movement of arm 16 and the operation of x-ray source assembly 26 and detector assembly 30 are governed by a control mechanism 52 of system 10. Controller, or control mechanism, 52 includes an x-ray controller 54 that provides power and timing signals to x-ray source 28 and a motor controller 56 that controls the position of arm 16, source assembly 26 and detector assembly 30.

In the example embodiment, a data acquisition system (DAS) 58 in control mechanism 52 samples data from detector 32 for subsequent processing. An image processor/reconstructor 60 (the term reconstructor as used herein includes reconstructors as are known in the computed tomography art, as well as processors for processing data collected in a scan (i.e., not limited to computed tomography image reconstructors)) receives sampled x-ray data from DAS 58 and performs high speed image processing/reconstruction. The resultant image is applied as an input to a computer 62 which stores the image in a mass storage device 63.

Computer 62 also receives commands and scanning parameters from an operator via a console 64 that has a keyboard. One or several associated displays 66 allows the operator to observe the resultant image and other data from computer 62. The operator supplied commands and parameters are used by computer 62 to provide control signals and information to DAS 58, x-ray controller 54 and motor controller 56. Computer 62 operates a table motor controller 68 which controls position of motorized table 46 relative to system 10.

In one embodiment, the user input device comprises multiple capacitance sensors located on base 14, source assembly 26, detector 32, positioning arm 16, and table 46. Each sensor yields information about the proximity of the operator (e.g. operator's hand) and other objects (e.g. patient body) relative to the sensor. The information from each sensor is processed (e.g., by computer 62) using a vector addition algorithm, as described below.

Figure 2:
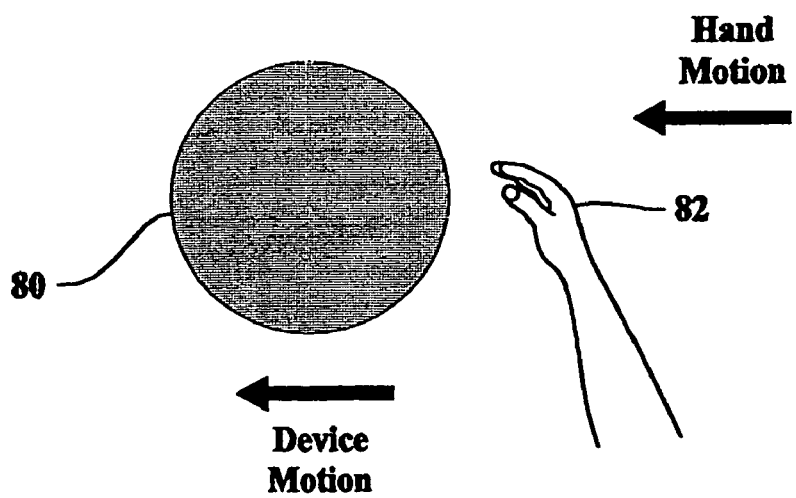
FIG. 2 is a schematic illustration of hand motion and device motion.

More specifically, the general principles of the vector addition algorithm are described below with respect to FIGS. 2, 3, and 4. Referring to FIG. 2, there are no external obstacles illustrated, and the objective is to move a device 80 as an operator's hand 82 approaches device 80. Device 80 moves directly away from operator's hand 82. The closer hand 82 is to device 80, the faster device 80 moves away from hand 82. The operation becomes slightly more complicated as the potential for external objects, or the control of multiple operators, becomes possible. These more complicated cases are illustrated in FIGS. 3 and 4.

Figure 3:
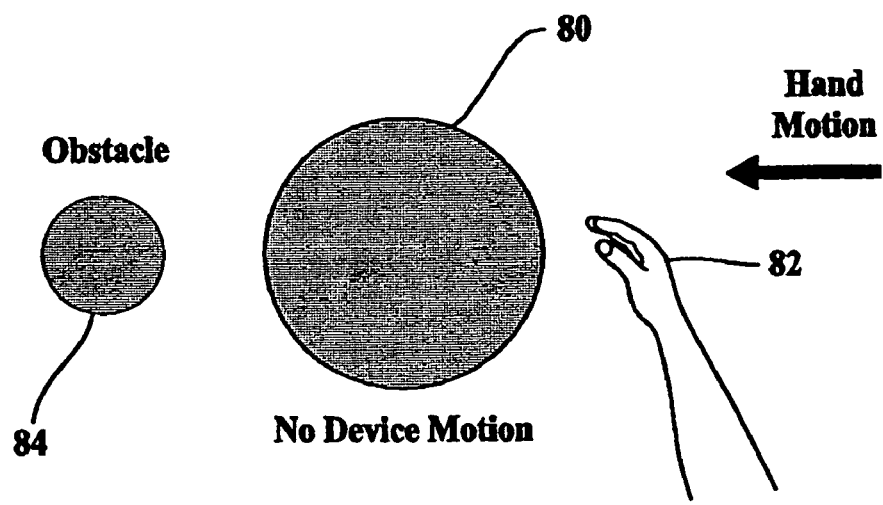
FIG. 3 is a schematic illustration of hand motion and intended device motion with an obstacle.

In FIG. 3, the operator is requesting that device 80 move away from hand 82, yet move directly into an obstacle 84. The system should respond by moving away from hand 82, and then slowing down as device 80 approaches obstacle 84. Eventually, device 80 should find an equilibrium position between hand 82 and obstacle 84 without directly contacting either hand 82 or obstacle 84.

Figure 4:
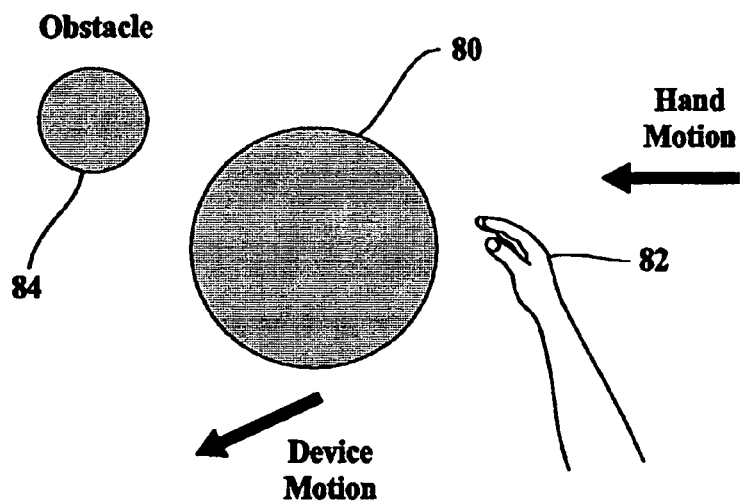
FIG. 4 is a schematic illustration of hand motion and compensated device motion with an obstacle.

FIG. 4 illustrates a case in which there is a trajectory along which device 80 can move while satisfying the operators request to "move left" while simultaneously avoiding obstacle 84. In order accomplish the functionality illustrated in FIGS. 3 and 4, both the location and proximity of various objects along the device periphery should be known.

Although the illustrations in FIGS. 2, 3, and 4 appear two-dimensional, the principles can be easily generalized to three-dimensional applications depending on the functionality of the system to be controlled.

Figure 5:
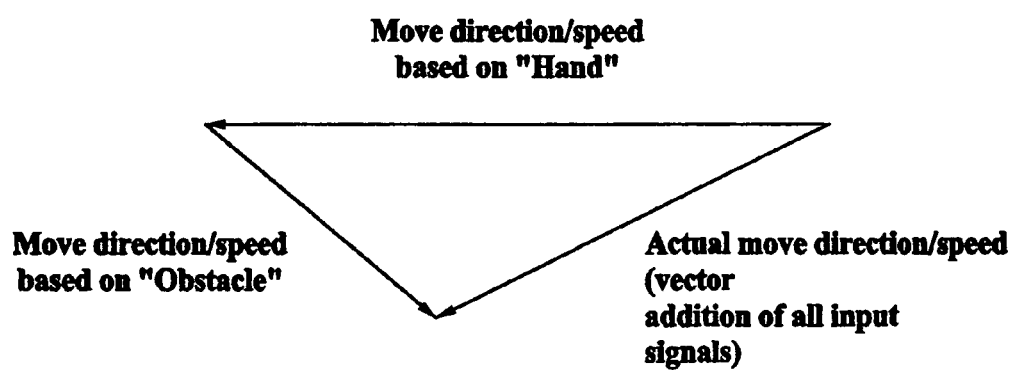
FIG. 5 is a vector illustration of movement.

FIG. 5 is a vector representation of accomplishing the movement illustrated in FIG. 4. Specifically, the output of each proximity sensor is used to calculate the speed and direction of a move given the proximity of objects. The direction of the move for a particular sensor is based on the orientation of that sensor and it is assumed that the sensor output is a scalar quantity (e.g. a voltage or single integer). Multiple sensors are attached to the device to provide the desired spatial resolution and coverage of the device. The output from each sensor, which consists of a signal strength (representative of speed) and a direction based on the orientation of each sensor, is then added vectorially to create a composite move vector. This composite move vector accounts for surrounding objects. Such vector addition is implemented in software, firmware or dedicated hardware. The device is then commanded to move with the speed and direction of this composite move vector. For example, the vectors which control movement of the particular device are controlled so that the movement is consistent with the composite move vector.

Set forth below are descriptions of two embodiments of capacitance sensor arrangements, sometimes referred to herein as user input devices. One embodiment is referred to as an "8-segment" sensor arrangement, and the other embodiment is referred to as a "32-segment" sensor arrangement. Both embodiments are two-dimensional and sense object proximity in a single plane. More particularly, the 8-segment sensor arrangement detects object proximity, while the 32-segment sensor arrangement detects "touch". Therefore, while the 8-segment sensor arrangement uses the vector addition algorithm previously described, the 32-segment sensor arrangement assumes that vectors have a length of either 0 or 1 depending on whether a particular sensor is touched (1) or not touched (0). The sensors are configured to couple to medical equipment. As used in this context, the "configured to couple" means attached to, directly or indirectly.

Figure 6:
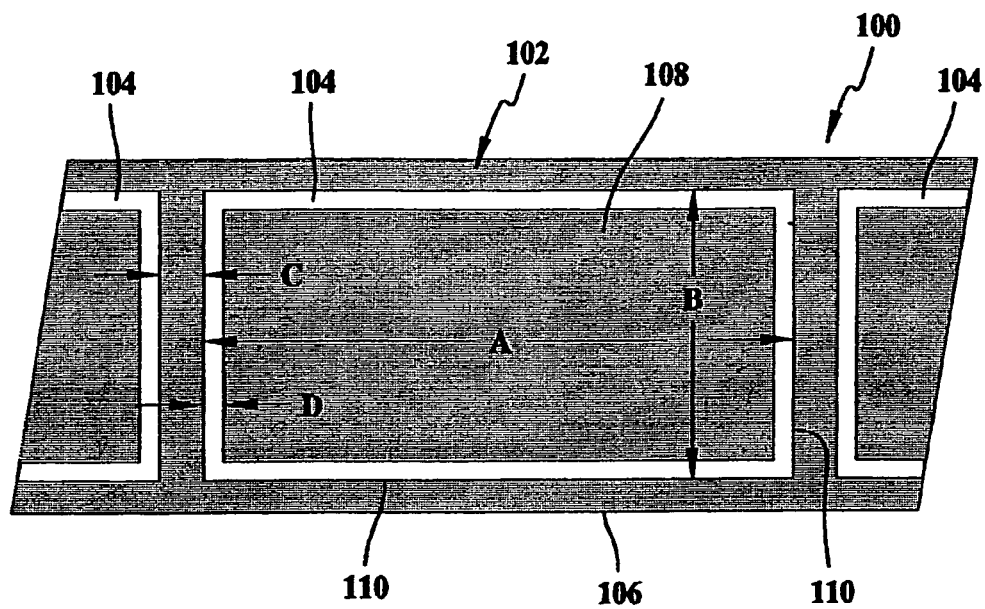
FIG. 6 illustrates one example segment in an 8-segment sensor arrangement.

Referring to FIG. 6, and regarding an 8 segment sensor arrangement 100, a portion of a core which comprises a circular plastic (e.g., an ABS plastic) ring 102 with a nominal outside diameter of 32 cm is illustrated. Alternatively, the core could be rectangular. The circular shape is the same size as the exterior of the 20 cm X-ray image intensifier used on vascular X-ray imaging products commercially available from GE Medical Systems. Milwaukee, Wis., of General Electric Company. Eight sensor segments 100 are secured to an exterior surface 106 of ring 102, with each sensor 104 covering a nominally 45° segment. Each 45° segment is divided into a primary sensing area 108, and a periphery 110 of each segment is covered with a ground plane. The ground plane minimizes cross-segment sensitivity and electrical cross talk between segments. The ground plane also localizes the sensing area, so those objects outside the desired sensing area are not detected. The material shown in FIG. 6 is a thin copper foil bonded to the ring. Example dimensions are: A=5.13 inches, B=2.6 inches, C=0.36 inches, and D=0.125 inches.

Figure 7:
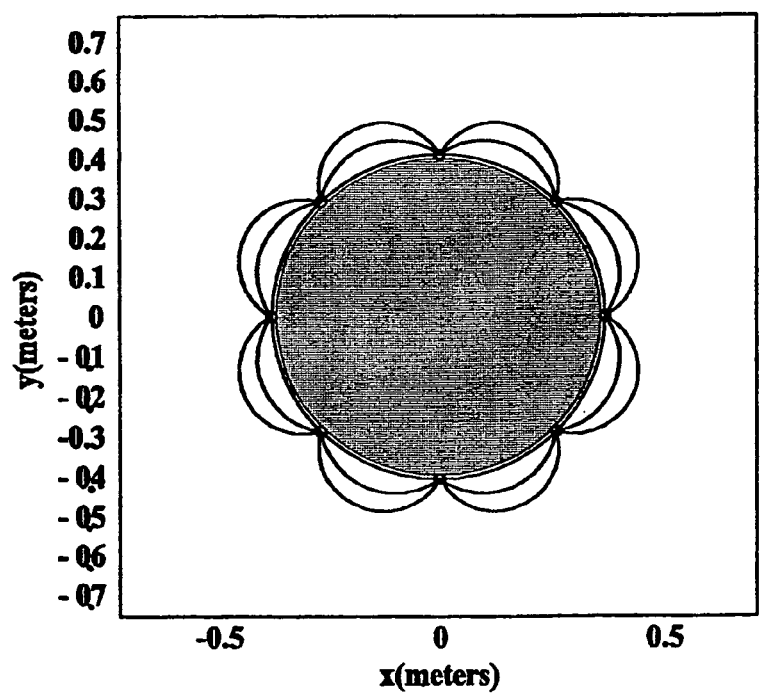
FIG. 7 is a graph illustrating a nominal finite element analysis for the 8-segment sensor arrangement.

In the example embodiment, the sizes of each segment and ground planes were chosen based on a nominal finite element analysis shown in FIG. 7. The sensor has a sensitive area between 3 and 5 cm away from the exterior surface.

Figure 8:
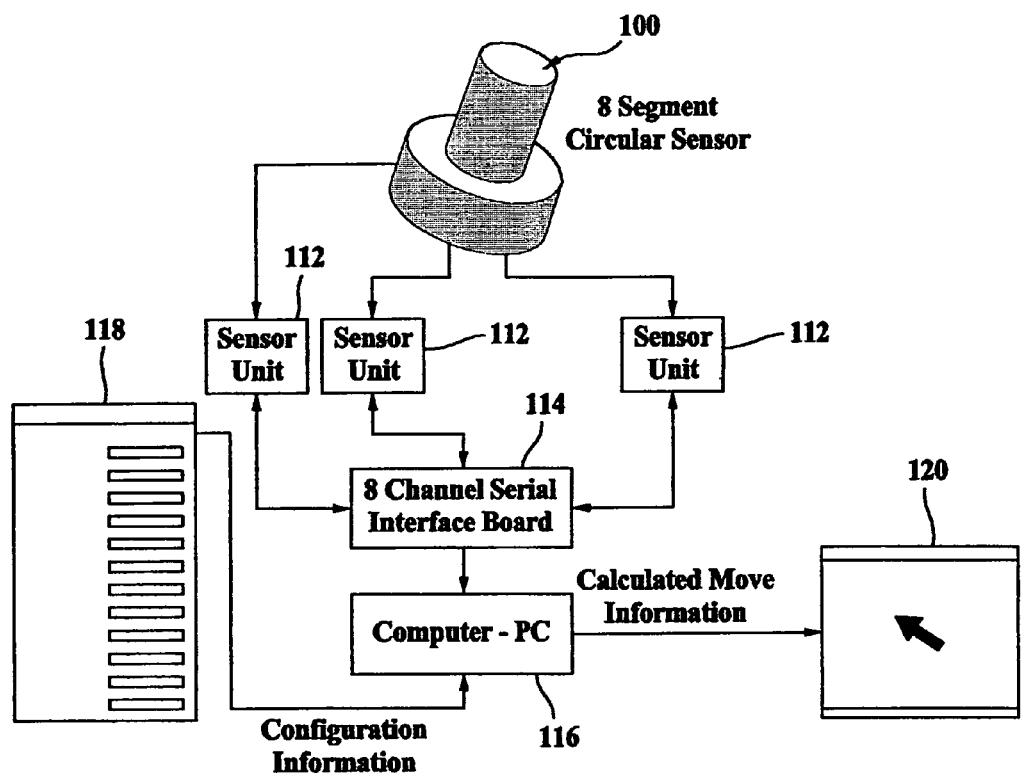
FIG. 8 is a schematic illustration of an 8-segment sensor arrangement control circuit.

Each sensing area is connected to capacitive sensor electronics as shown in FIG. 8. The sensor arrangements include capacitive units 112 which, in one embodiment, are model QT9701B-S sensor units commercially available from Quantum Research Group, United Kingdom. Each sensor unit 112 is coupled, via an 8 channel serial interface 114 with an RS232 communications link, to a processor, illustrated as a personal computer (PC) 116. Of course, other communication links can be used. The processor need not be a PC, however, and can be any device capable of performing the processing functions described below. The QT9701B-S sensor unit also contains approximately 20 configurable parameters, which can be configured over the serial communications link. The software configuration interface ensures that all eight QT9701B-S sensor units are configured identically so that the sensor sensitivity is uniform around the sensor periphery. In some applications, a non-uniform sensitivity may be desired, and either sensor units 112 can be configured differently, or the signal from each sensor unit 112 on processor 116 can be interpreted differently.

In FIG. 8, a software interface 118 for displaying configuration information on personal computer 116 also is illustrated. Rather than actually connecting 8-segment sensor 100 to imaging equipment, the speed and direction of move information is computed using the vector addition algorithm. An arrow displayed on a PC display 120 then indicates the direction of the computed move. The speed of the computed move is represented by the size of the arrow, with a larger arrow representing a higher speed. Thus, information about both the direction and speed that the imaging equipment would move in response to people and objects is displayed, while not requiring the complete imaging system.

Sensor units 112 operate autonomously, with no synchronization between the sensor excitation/readout. Of course, for a synchronized implementation, integrated electronics would facilitate synchronization between the excitation and measurement of each sensing segment, and therefore further reduce cross-channel interference and sensitivity.

Regarding the 32-segment sensor arrangement, like the 8-segment embodiment described above, a ring with a nominal outside diameter of 32 cm is utilized. In the example embodiment, the capacitive sensor units used are model QT60320 sensor units, commercially available from Quantum Research Group, United Kingdom. These sensor units are generally known as capacitance based matrix touch switches.

The QT60320 sensor unit detects the capacitive coupling of electromagnetic fields. The matrix switch can be envisioned as 4 rows and 8 columns of "wires". The intersection of a particular row with a particular column is a "switch", though electrically there is no true intersection of the rows with the columns. Each of these wires is excited by the electronics and creates an electromagnetic field. When a finger, hand, or other object is placed in close proximity of any intersection, the electromagnetic field of the corresponding row and corresponding column are coupled, and this particular "switch" is turned ON. The output of the sensor at any given time is the state of all of the 32 switches formed by the intersection of the 4 rows and 8 columns. Unlike some "touch switches", the QT60320 sensor does not require passing electrical "leakage" currents through the object being detected. Thus, the conductive wire or foil matrix can be completely enclosed behind glass, plastic, or other material that is not electrically conductive. A true "touch", meaning direct contact to the conductive components, is not required. The switch is known as a touch switch because close proximity is required, and for practical purposes this may be indistinguishable from a touch, though electrically this non-contact technique has safety (e.g. freedom from electrical leakage currents) and reliability advantages (e.g. immunity to electrostatic discharge).

Figure 9:
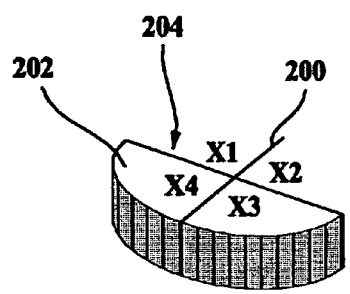
FIG. 9 illustrates a capacitance based matrix touch switch.
Figure 10:
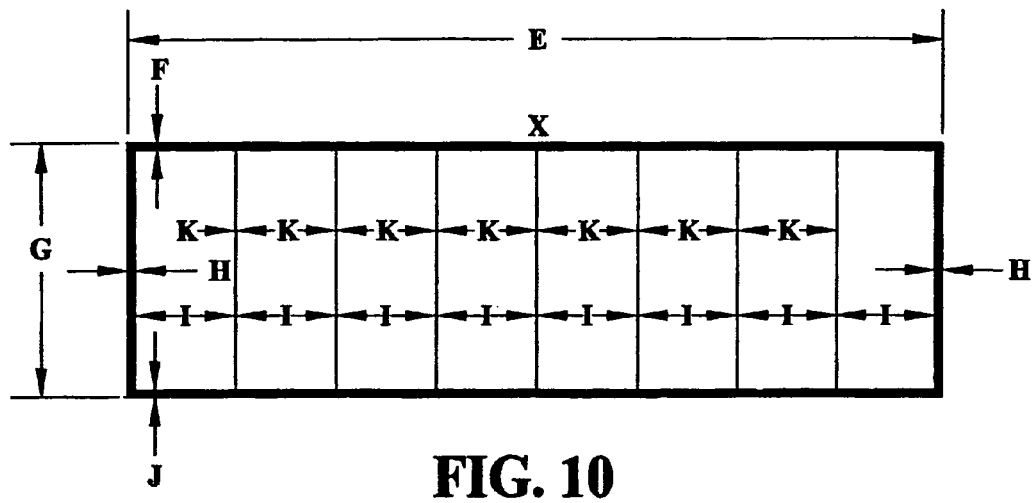
FIG. 10 illustrates a sample segment of the switch shown in FIG. 9.

Referring to FIG. 9, a sensor 200 includes a conductive matrix 202 arranged around the periphery of a 32 cm diameter core, illustrated as a plastic ring 204. The 4 "rows" correspond to 4 circular segments, each covering a nominally 90° arc and denoted by "X", as shown in FIG. 10, which illustrates an "X" segment (covers 90°). Example dimensions are: E=27.52 cm, F=5 mm, G=8 cm, H=2 mm, I=3.3 cm, J=5 mm, and K=0.5 mm.

Figure 11:
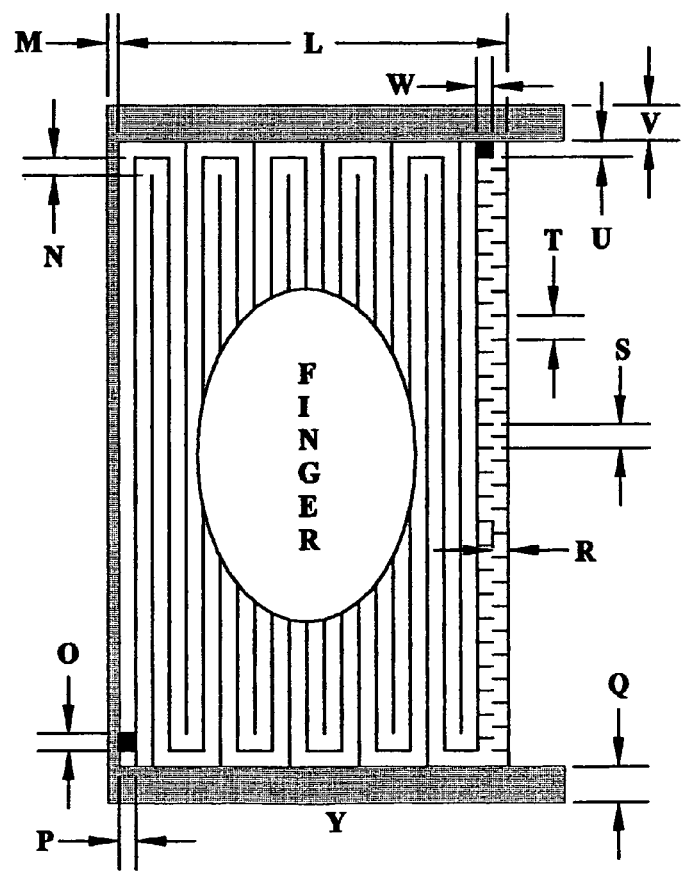
FIG. 11 is an exploded view of a segment of the switch shown in FIG. 10.

Referring to FIG. 11, within each 90° arc, there are eight smaller segments each covering a nominally 11.25° arc and labeled as "Y". Example dimensions are: L=3.3 cm, M=2 mm, N=3 mm, O=1.5 mm, P=1 mm, Q=5 mm, R=1 mm, S=2.5 mm, T=2.5 mm, U=1 mm, V=5 mm, and W=1.5 mm.

Each Y segment has a serpentine shape that is intertwined among "fingers" from the X segment. When an object such as a hand or finger (labeled FINGER in FIG. 11) comes into close proximity with the sensor surface, the object typically covers several of the X "fingers", and thus couples the electromagnetic fields of the corresponding X and Y segments. This coupling of electromagnetic fields closes, or turns ON, the switch associated with the intersection of the corresponding X and Y segments.

Figure 12:
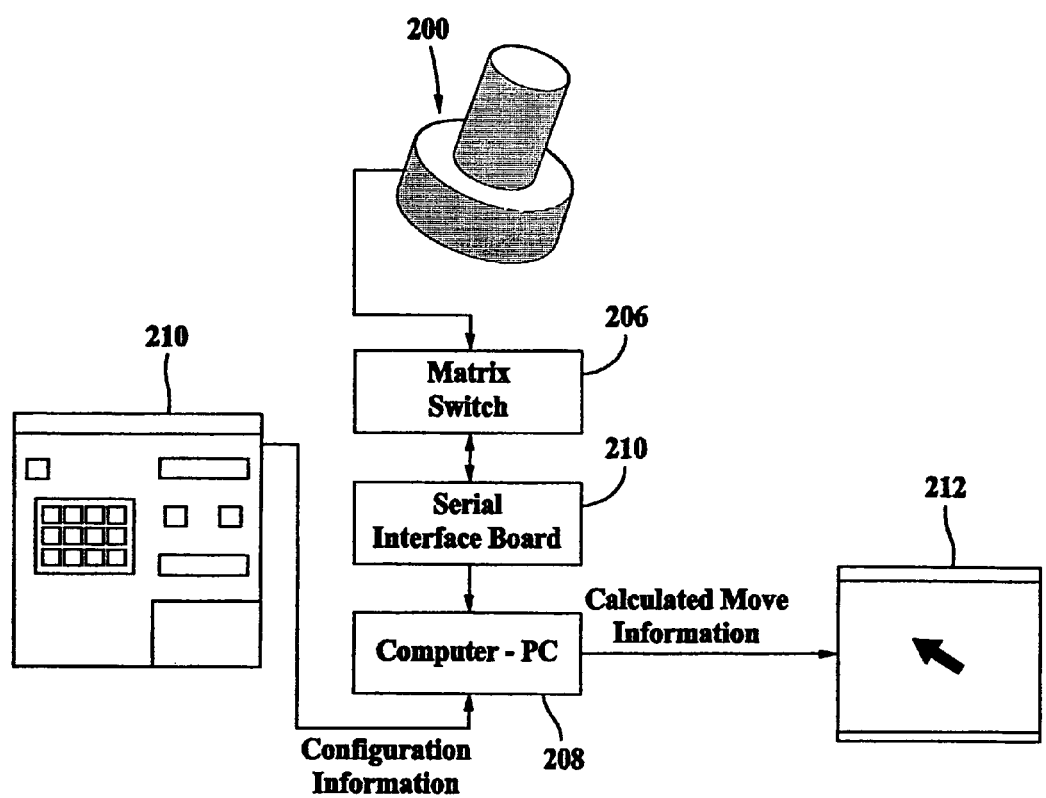
FIG. 12 is a schematic illustration of a 32-segment sensor arrangement control circuit.

FIG. 12 is a schematic illustration of a sensing circuit arrangement for 32-segment sensor 200. Sensor 200 is coupled to a matrix switch 206, which in the example embodiment is the QT 60320 switch commercially available from Quantum Research Group, United Kingdom. Switch 206 is coupled to a processor illustrated as a personal computer (PC) 208 via a serial (RS232) interface board 210. Of course, other communication links can be used. The processor need not be a PC, however, and can be any device capable of performing the processing function described herein in connection with the PC. Personal computer 208 configures and calibrates switches 206. Nominally, each switch is identically configured to provide uniform sensitivity. However, different switches may be configured differently depending on the particulars of the application, or to account for variability in different "switches" if the geometry of the "switches" is different. The output of sensor 200 is the discrete status (i.e. ON or OFF) of each of the 32 switches. This information is read approximately every 50 ms and processed by personal computer 208. The ON/OFF information from each switch is processed on the personal computer using the vector addition algorithm described above. Switch status is displayed on a display 212 of computer 208.

Unlike the 8-segment prototype, the 32 segment arrangement does not provide distance information about surrounding objects. Thus the vector addition algorithm involves adding the angles of those "switches" which are on, and computing the direction of the move based on this angular information. The speed of the move is some nominal value appropriately chosen for the equipment being controlled.

In FIG. 12, a display 212 of the move direction as computed by the vector addition algorithm is shown. Such display 212, of course need not be present. The direction of the motion would be in the direction as indicated by the arrow.

While the invention has been described in terms of various specific embodiments, those skilled in the art will recognize that the invention can be practiced with modification within the spirit and scope of the claims.

The invention claimed is:

1. A sensor comprising a core having an outer surface, a plurality of sensing areas on said outer surface, each said sensing area responsive to at least one object within a sensory field of said sensor, wherein the at least one object comprises at least one of an operator input representative of a desired movement of said movable member and an obstacle in proximity with said movable member.

2. A sensor according to claim 1 wherein said core comprises plastic, and wherein each of said sensing areas comprises a conductive foil bonded to said plastic.

3. A sensor according to claim 1 wherein said core has one of a circular and rectangular cross sectional shape.

4. A sensor according to claim 1 wherein a ground plane is at a periphery of each sensing area.

5. A sensor according to claim 1 wherein the operator input is based on a position of an operator's hand.

6. A sensor according to claim 1 further comprising eight sensing areas, each of said sensing areas comprising a conductive foil, and ground planes at a periphery of each said sensing area.

7. A sensor according to claim 1 further comprising thirty two sensing areas, each sensing area coupled to a matrix switch.

8. A sensor according to claim 1 wherein said sensors comprise at least one of a capacitance sensor, an infrared sensor, and an ultrasonic sensor.

9. A sensor according to claim 1 wherein said sensor determines both a speed and a direction in which the equipment is to be moved.

10. A sensor according to claim 1 wherein at least some of said sensors comprise capacitance sensors, each of said capacitance sensors being one of a proximity sensor and a touch based sensor.

11. A sensor according to claim 1 wherein said sensor is responsive to a position and speed of an operator's hand with respect to said sensor.

* * * * *